United States Patent [19]

Schuster et al.

[11] 4,157,709

[45] Jun. 12, 1979

[54] PROBE FOR OBTAINING CERVICAL MUCUS AND PROCESS THEREOF

[75] Inventors: Samuel R. Schuster, Wellesley; Louis Kopito; Harold Kosasky, both of Brookline, all of Mass.

[73] Assignee: Ovutime, Inc., Brookline, Mass.

[21] Appl. No.: 795,097

[22] Filed: May 9, 1977

[51] Int. Cl.² .............................................. A61B 10/00
[52] U.S. Cl. ..................................... 128/759; 128/269
[58] Field of Search .............. 128/2 B, 2 W, 263, 4–8, 128/127, 130, 131, 269, 304; 73/53

[56] References Cited

U.S. PATENT DOCUMENTS

| | | | |
|---|---|---|---|
| 1,703,216 | 2/1929 | Wappler | 128/6 |
| 2,022,065 | 11/1935 | Wappler | 128/6 |
| 2,184,642 | 12/1939 | Glass | 128/303.12 |
| 2,579,849 | 12/1951 | Newman | 128/3 |
| 3,877,464 | 4/1975 | Vermes | 128/2 W X |
| 3,924,608 | 12/1975 | Mitsui | 128/2 B |
| 3,960,143 | 6/1976 | Terada | 128/4 |
| 4,013,066 | 3/1977 | Schuster | 73/53 X |
| 4,023,559 | 5/1977 | Gaskell | 128/2 W |

OTHER PUBLICATIONS

Medical Surgical Review, p. 35, (Advertisement), Feb. 1970.

*Primary Examiner*—Robert W. Michell
*Assistant Examiner*—Francis J. Jaworski
*Attorney, Agent, or Firm*—Morse, Altman, Oates & Bello

[57] ABSTRACT

A probe is provided for inserting a test element into the vaginal cavity while shielding it from intermediate vaginal contact, for positioning the test element precisely in contact with the cervical os in order to collect a specimen of cervical material therefrom, and for retrieving the test element and the specimen from the vaginal cavity while shielding them from intermediate vaginal contact. Processes are provided for retrieving specimens in the form of tissue or mucus.

14 Claims, 13 Drawing Figures

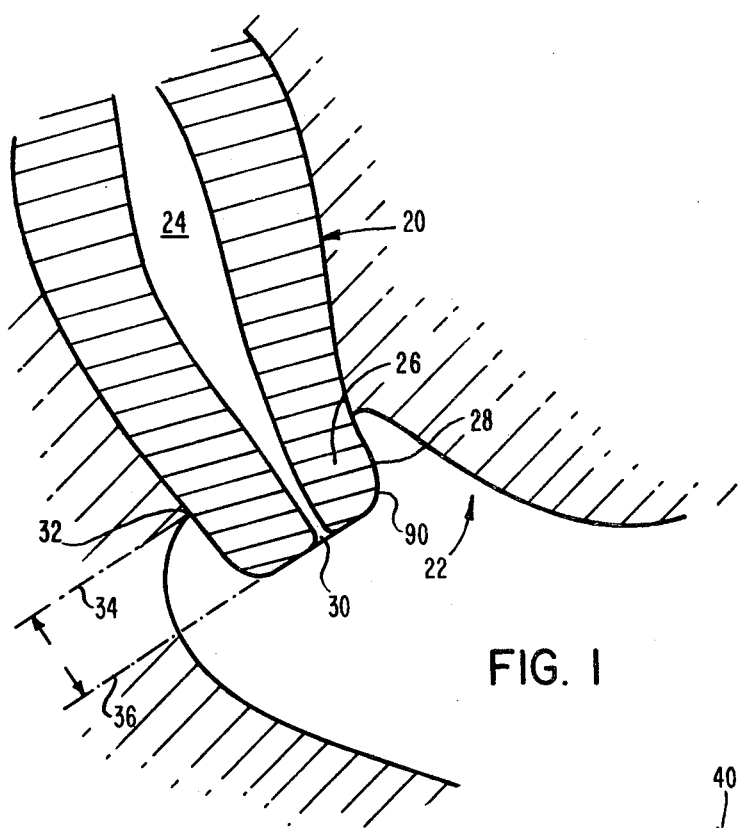
FIG. 1
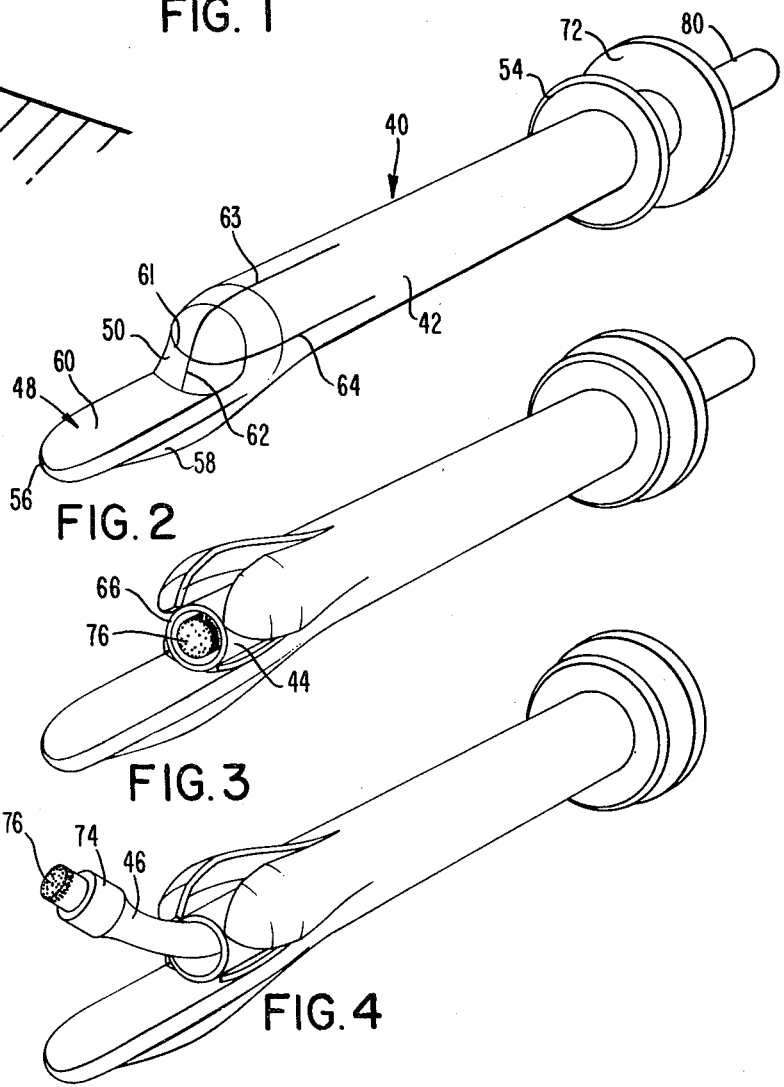
FIG. 2
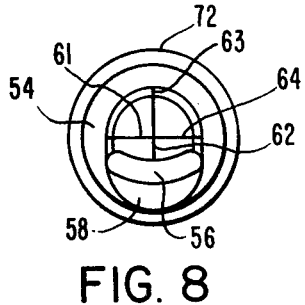
FIG. 8
FIG. 3
FIG. 4

PROBE FOR OBTAINING CERVICAL MUCUS AND PROCESS THEREOF

BACKGROUND OF THE INVENTION

1. Field of the Invention

The present invention relates to the medical testing of cervical material, i.e. tissue and/or mucus, and more particularly to the routine collection of cervical material via the vaginal cavity in such a way that the cervical specimen is unaffected by contact with the vaginal wall.

2. The Prior Art

In the past, it usually has required skilled medical personnel to obtain useful samples of cervical material. In one form, such cervical material is tissue from the cervical os, which is tested for malignancy in the form of a pap smear. In another form, such cervical material is mucus from the cervical os, which indicates ovulation when of predeterminedly low viscosity and the absence of ovulation when of predetermined high viscosity, for fertility control. Previously proposed probes, by which cervical material may be collected, examined and tested, generally have not been for self-use by women wishing to retrieve cervical specimens. It is desired to retrieve such cervical specimens by a reliable probe, which does not require a skilled medical operator but rather which can be operated by the subject woman herself. The probe of the present invention thus enables any woman to submit self-obtained cervical tissue specimens to the laboratory for microscopic examination or to subject self-obtained cervical mucus to rheological testing in simple equipment available in the home for fertility control.

BRIEF DESCRIPTION OF THE INVENTION

The primary object of the present invention is to provide a probe for inserting a test element into the vaginal cavity while shielding it from intermediate vaginal contact, for positioning the test element precisely in contact with the cervical os in order to collect a specimen of cervical meterial, and for retrieving the test element and the specimen from the vaginal cavity while shielding them from intermediate vaginal contact. The design of this probe is based in part upon two considerations. The first consideration is that, in most women, the distance between the cervical os and posterior fornix is approximately the same, viz. 1 to 5 centimeters. The second consideration is that, in order to achieve the most accurate test results, it is often desirable that the cervical material be undisturbed by transfer from one mechanical device to another, for example from a first test support to a second test support. It is desirable particularly that the collection of cervical mucus, which at times other than during mid-cycle is very sparse, may be made directly on the final test support. In accordance with the present invention, the probe preferably comprises a test element for collecting a specimen by direct contact with the cervical os, a sheath within which the test element is confined during insertion into the vaginal cavity, a foot at the forward extremity of the sheath, which enables repeated positioning of the sheath predeterminedly within the vaginal cavity, and a manual control for directing the test support from within the sheath into contact with the cervical os and from contact with the cervical os back into the sheath. Thus, removal of the instrument from the vaginal cavity achieves isolation of the test support within the sheath during removal of the sheath from the vaginal cavity.

Other objects of the present inventions will in part be obvious and will in part appear hereinafter.

The invention accordingly comprises the devices and processes herein disclosed, together with their parts, steps and interrelationships, the scope of which will be indicated in the appended claims.

BRIEF DESCRIPTION OF THE DRAWINGS

For a fuller understanding of the nature and objects of the present invention, reference is made to the following detailed description, which is to be taken in connection with the accompanying drawings, wherein:

FIG. 1 is a sagittal view of the human female anatomy in the vicinity of the cervix;

FIG. 2 is a perspective view of a device embodying the present invention in a first operative condition;

FIG. 3 is a perspective view of the device of FIG. 2 in a second operating condition;

FIG. 4 is a perspective view of the device of FIG. 2 in a third operating condition;

FIG. 8 is a front view of the device as shown in FIGS. 2 and 5;

DETAILED DESCRIPTION OF THE PREFERRED EMBODIMENTS

Figure 5:
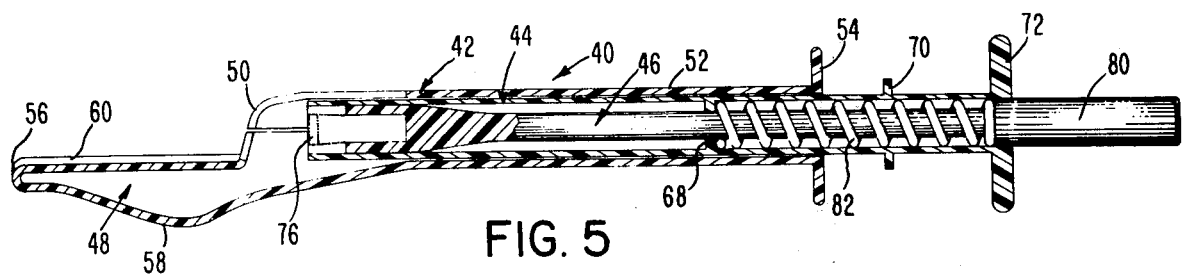
FIG. 5 is a longitudinal, cross sectional view of the device as shown in FIG. 2.

FIG. 1 anatomically illustrates details of the uterus 20 and the vaginal wall 22. Uterus 20 includes the uterine fundus 24, the cervix 26, the portio vaginalis 28 and the cervical os 30. The posterior fornix 32 between the most distal portion of the portio vaginalis and the posterior vaginal wall is of particular interest in accordance with the present invention. It has been found that the geometrical distance, between a plane 34 containing the end of the posterior fornix and a plane 36 containing the cervical os, ranges from 1 to 5 centimeters in almost all normal women. The test probe now to be described relies upon that anatomical fact.

Figure 9:
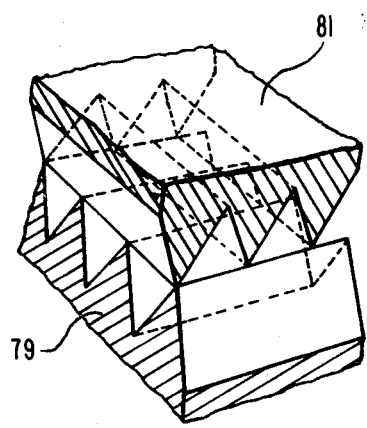
FIG. 9 is a perspective view of a component of the device of FIGS. 2 to 7, in operative relation to a component of a test apparatus.

With reference now to FIGS. 2 and 5, the illustrated probe, shown generally at 40, comprises an outer sheath 42, an intermediate tube 44 slidable therewithin and an inner shaft 46 slidable therewithin. Sheath 42, tube 44 and shaft 46, in effect, are outer, intermediate and inner telescoping members, all of which are predeterminally shaped to serve interrelated functions. The purpose of these interrelated functions is to collect mucus from the cervical os on a test support 76, which, as shown in FIG. 9, is in the from of a ridged element 79 that is adapted for contact by a cross-ridged element 81 in such a way that the pulling force necessary to cause separation of the ridged elements is a function of rheological properties. Such a system is described in detail in U.S. Pat. No. 3,926,037, issued Dec. 16, 1976 and U.S. Pat. No. 4,002,056, issued Jan. 11, 1977.

Sheath 42, which is composed of a thin semi-rigid polymer, such as polyethylene or polyethylene terephtalate, includes a forwardly projecting reference foot portion 48, a transversely shaped intermediate mouth portion 50, a rearwardly extending tubular body portion 52, and a rearward flange poriton 54.

In accordance with the present invention, reference foot portion 48 ranges in length from 1 to 5 centimeters so that, when the instrument is inserted into the vagina, the reference foot portion moves along the inferior vaginal wall until seated in the posterior fornix, which serves as a reference point that limits further insertion. Reference foot portion 48 has a narrow forward extremity 56 that is shaped to contact the end 32 of the posterior fornix, a convex under surface 58 that is shaped to rest against the posterior vaginal wall and a concave upper surface 60 that is shaped to rest beneath the most distal portion of the portio vaginalis. Intermediate mouth portion 50 includes an upwardly directed surface that is severed into sections by intersecting slits 61, 62, 63, 64, which extend longitudinally along body portion 42 and meet in the vicinity of the center of mouth portion 50. These severed sections constitute a mouth with flexible flaps that tend to remain closed normally but that can be opened from inside the sheath in a manner to be described below.

Figure 6:
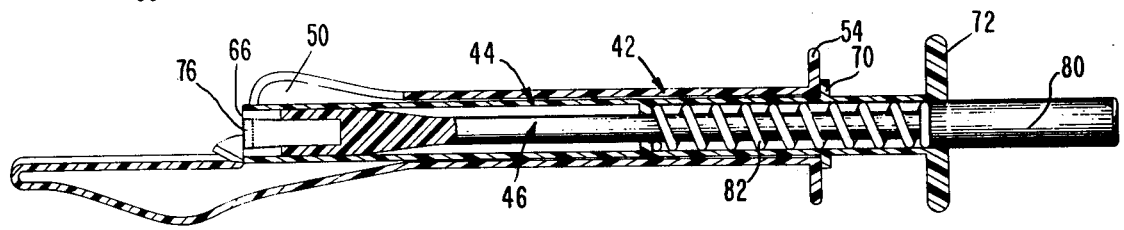
FIG. 6 is a longitudinal, cross sectional view of the device as shown in FIG. 3.
Figure 7:
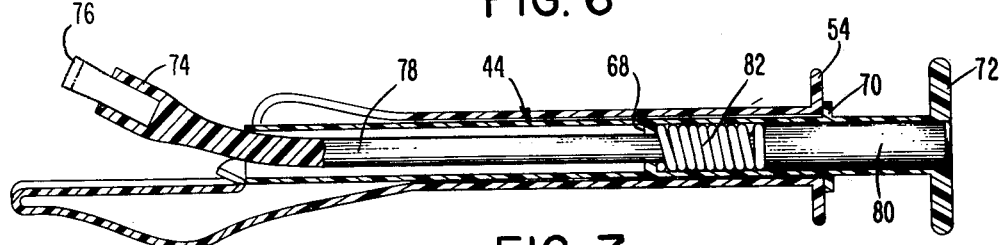
FIG. 7 is a longitudinal, cross sectional view of the device as shown in FIG. 4.

Intermediate tube 44 has an outside diameter that is slightly less than the inside diameter of body portion 52 of sheath 42 so as to be slidable within body portion 52. Tube 44 has an open forward end 66, an intermediate inwardly directed annular rib 68, an outwardly directed stop flange 70 and an outwardly directed manual flange 72. As shown in FIGS. 3 and 6, when flange 70 of tube 44 is in abutment against flange 54 of sheath 42, forward extremity 66 of tube 44 projects through mouth portion 50 to expose the front end of inner shaft 46. It will be observed that, when in the condition shown in FIGS. 2 and 5, sheath 40 is capable of being inserted through the vaginal cavity so that extremity 48 seats against end 32 of the posterior fornix and so that mouth portion 50 is adjacent to cervical os 30. Preferably tube 44 is composed of a semi-rigid material such as polyethylene or polyethylene terephthalate.

Shaft 46 includes: a forward portion 74, which is recessed to seat a test element 76; a body portion 78, which slides within annular rib 68; and a rearward handle portion 80 that slides within tube 44. The outside diameter of body portion 78 is slightly less than the inside diameter of annular rib 68. The outside diameter of rearward handle 80 is slightly less than the inside diameter of tube 44. The forward portion of shaft 78 has a natural curve which causes it to bend upwardly when it is not confined within tube 44. When rearward portion 80 of shaft 46 is pressed inwardly against the bias of compression spring 82, the forward face of test support 76 is pressed against cervical os 30. Preferably shaft 46 is composed of a semi-rigid material such as polyethylene or polyethylene terephthalate.

OPERATION

In operation, first device 40, as shown in FIG. 2, is inserted into the vaginal cavity in such a way the reference foot portion 48 moves continuously along the inferior vaginal wall until the instrument can be inserted no farther. At this point, forward extremity 56 is seated at the end 32 of the posterior fornix, which is the reference point for operation of the instrument. Next, manual pressure is exerted between fingers against flange 54 and thumb against flange 72 to cause flange 70 to abut against flange 54 and forward extremity 66 of tube 44 to project through mouth 50. Next, manual pressure on rearward portion 80 of shaft 46 against the bias of spring 82 causes the forward portion of shaft 46 to project from tube 44 and a forward surface of test support 76 to abut against cervical os 30. Next, the pressure on rearward portion 80 of shaft 46 is released to permit spring 82 to retract forward portion 74 and test support 76 into tube 44. Then, tube 44 is retracted so that its forward portion recedes through mouth 50 of sheath 52. Finally, the entire device is removed from the vaginal cavity. The arrangement is such that test support 76 now can be removed from within the device in such a way as to permit cervical mucus thereon to be tested.

Figure 10:
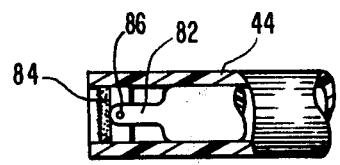
FIG. 10 is a side view of a modification of a component of the device of FIGS. 2 to 7, in a first operating condition.
Figure 11:
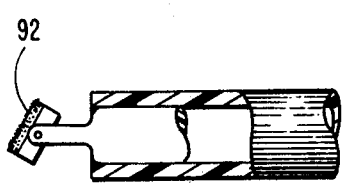
FIG. 11 is a side view of a component of FIG. 9, in a second operating condition.

A modification of a component of the device of FIGS. 3 to 7 is shown in FIGS. 10 and 11. FIGS. 10 and 11 show the forward extremity of a shaft 82 which can be substituted for shaft 46, of the above described embodiment. Here shaft 82, which does not have a natural curved forward portion, is straight and has at its forward extremity a test element 84. Test element 84 is pivoted to shaft 82 at 86. Test element 84 is of sufficiently small cross sectional dimension to slide with the end of shaft 82 into and out of tube 44. When test element 84 is projected forwardly into contact with the anterior lip 90 of the portio vaginalis, it pivots in a clockwise direction in such a way that its test surface 92 contacts cervical os 30. When in this operative condition, test surface 92 collects cervical mucus or tissue from the cervical os. The operation of the illustrated device with the modification shown in FIGS. 10 and 11 is substantially the same as the operation of the embodiment of FIGS. 2 to 7 described above.

Figure 12:
FIG. 12 is a side view of another modification of a component of the device of FIGS. 2 to 7, in a first operating condition.
Figure 13:
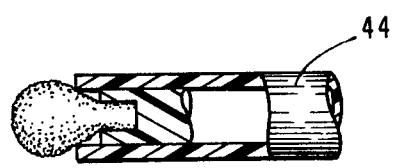
FIG. 13 is a side view of the component of FIG. 12, in a second operating condition.

In another modification, as shown in FIGS. 12 and 13, test element 76 is replaced by a sponge 94 that is composed of a resilient polymeric foam. The sponge is sufficiently resilient to expand when protruded from tube 44 and to contract when retracted into tube 44. Sponge 94 is designed to abrade the cervix in the vicinity of the os in such as way that, when rotated as in FIG. 13, its serrated surface scrapes and collects tissue for later microscopic examination. The operation of this modification is otherwise substantially the same as the operation of the embodiment of FIGS. 2 to 7 described above.

Since certain changes may be made in the foregoing disclosure without departing from scope of the invention hereof, it is intended that all matter described in the foregoing specification or shown in the accompanying drawings be interpreted in an illustrative and not in a limited sense.

What is claimed is:

1. A vaginal probe comprising:
   (a) sheath means characterized substantially by an original shape extending substantially along an axis of elongation for insertion into the vaginal cavity, said sheath means including forward extremity means connected thereto and intermediate mouth means, said sheath means being sufficiently rigid to substantially maintain said original shape during said insertion;

(b) control means causing closing of said mouth means when in one condition and causing opening of said mouth means when in another condition;

(c) specimen sampling means for confinement within said sheath means when in one condition and for protrusion through said mouth means when in another condition; said specimen sampling means extending through a curvature when in said other condition, from said mouth means to the cervical os (d) said specimen sampling means being confined within said sheath means when said sheath means is inserted into and is withdrawn from the vaginal cavity;

(e) said specimen means being in contact with the cervical os when said extremity means is seated in the posterior fornix, said control means is in said one condition so that said mouth means is open, and said specimen means is in said one condition so that it protrudes through said mouth means;

(f) said forward extremity means having a configuration for seating in the posterior fornix and being a mechanical reference ranging in length along said axis from 1 to 5 centimeters and maintaining said length along said axis during said insertion.

2. The probe of claim 1 wherein said mouth means is provided by transverse portion that is integral with portions of said sheath means and that is defined by slits in said transverse portion.

3. The probe of claim 1 wherein said control means includes a tube slidable in said sheath means between an inoperative position at which it is confined within said sheath means and an operative position at which it protrudes through said mouth means.

4. The probe of claim 1 wherein said specimen means includes a rod having a test element at its forward extremity, said forward extremity having an inoperative position at which it is confined within said control means and an operative position at which it projects from said control means.

5. The probe of claim 1 wherein said specimen means includes an element with a ridged face for contacting the cervical os.

6. The probe of claim 1 wherein said specimen means includes a shaft and a pivoted element thereon, said pivoted element having a surface for contact with the cervical os.

7. The probe of claim 1 wherein said specimen means includes a sponge.

8. A vaginal probe comprising:

(a) a sheath and a forward extremity connected thereto for insertion into the vaginal cavity, said sheath including an intermediate mouth, said sheath and said extremity being composed of a resilient polymer and being developed along an axis, said mouth being generally transverse with respect to said axis, said sheath and said extremity being characterized by an original shape extending substantially along an axis of elongation and being sufficiently rigid to maintain said original shape during said insertion;

(b) a movable control within said sheath, said control causing closing of said mouth when in one condition and causing opening of said mouth when in another condition;

(c) a shaft having a test element at an end, said shaft being reciprocable with respect to said sheath, said test element being confined within said sheath when in one condition and being protruded through said mouth when in another condition; said shaft extending through a curvature when in said other condition from said mouth to the cervical os;

(d) said test element being confined within said sheath when said sheath is inserted into and is withdrawn from the vaginal cavity;

(e) said test element being in contact with the cervical os when said extremity is seated in the posterior fornix, said control is in said one condition so that said mouth means is open, and said test element is in said one condition so that it protrudes through said mouth;

(f) said extremity having a configuration for seating in the posterior fornix and being a mechanical reference ranging in length along said axis from 1 to 5 centimeters.

9. The probe of claim 8 wherein said mouth is provided by transverse portion that is integral with portions of said sheath and that is defined by slits in said transverse portion.

10. The probe of claim 8 wherein said tube is slidable in said sheath between an inoperative position at which it is confined within said sheath and an operative position at which it protrudes through said mouth.

11. The probe of claim 8 wherein said test element includes a rod, said forward extremity having an inoperative position at which it is confined within said tube and an operative position at which it projects from said tube.

12. The probe of claim 8 wherein said test element includes a ridged face for contacting the cervical os.

13. The probe of claim 8 wherein said test element includes a shaft and a pivoted element thereon, said pivoted element having a surface for contact with the cervical os.

14. The probe of claim 8 wherein said test element includes a sponge.

* * * * *